United States Patent [19]

Citron et al.

[11] 3,999,557
[45] Dec. 28, 1976

[54] PROPHYLACTIC PACEMAKER

[75] Inventors: Paul Citron, New Brighton; John M. Adams, Anoka, both of Minn.

[73] Assignee: Medtronic, Inc., Minneapolis, Minn.

[22] Filed: July 11, 1975

[21] Appl. No.: 595,001

[52] U.S. Cl. .................... 128/419 PG; 128/422
[51] Int. Cl.² ................................ A61N 1/36
[58] Field of Search .......... 128/419 PG, 421, 422

[56] References Cited
UNITED STATES PATENTS

| 3,717,153 | 2/1973 | Bowers | 128/419 PG |
| 3,805,796 | 4/1974 | Terry et al. | 128/419 PG |
| 3,807,410 | 4/1974 | Wall et al. | 128/419 PG |
| R28,003 | 5/1974 | Gobeli | 128/419 PG |

Primary Examiner—Robert W. Michell
Assistant Examiner—Lee S. Cohen
Attorney, Agent, or Firm—Lew Schwartz; Wayne A. Sivertson

[57] ABSTRACT

A demand pacemaker having different standby and pacing rates and circuitry for selectively rendering the standby and pacing rates substantially identical. First and second capacitors control the standby and pacing rates, respectively, one capacitor being responsive to either a natural heartbeat or a pacemaker output pulse to alter the rate established by the other. In a preferred embodiment, the second capacitor is charged during a pacemaker output pulse and discharges through the first capacitor to decrease its charging time, the charging time of the first capacitor controlling the pacemaker output pulse frequency. Circuitry responsive to externally generated signals causes the second capacitor to charge during both a natural heartbeat or a pacemaker output pulse to render the pacemaker standby and pacing rates substantially identical. In this manner, the pacemaker of the present invention may be employed to monitor heart activity at a first, or standby, rate while providing a pacing function at a second, higher rate, on demand, until such time as the necessity for the pacing function is established with the standby rate then being modified to conform to the pacing rate.

21 Claims, 2 Drawing Figures

PROPHYLACTIC PACEMAKER

BACKGROUND OF THE INVENTION

Hysteresis pacemakers, demand cardiac pacemakers having different pacing and monitoring (standby) rates, are known to the prior art. Such devices are employed to prevent the heartbeat rate from falling below a minimum frequency while pacing the heart at a higher frequency, when needed. In this manner, the complications which may result from a competition between a pacemaker and natural heart activity can be reduced while maintaining a heartbeat rate at a level capable of sustaining life. An example of a prior art demand pacemaker having different pacing and standby rates is disclosed in U.S. Pat. No. 28003 for Electronic Demand Heart Pacemaker With Different Pacing And Standby Rates, reissued May 7, 1974, which is hereby incorporated by reference.

It has been suggested in medical literature that patients having a high risk of sudden cardiovascular death would benefit from the implantation of a standard demand pacemaker. A pacemaker having different standby and pacing rates (i.e., hysteresis pacemaker) may be better suited for these high risk patients since it is less likely to interfere with normal heart rhythms and would only become activated when the patient's intrinsic heart rate becomes sufficiently low to justify pacing. Sudden cardiovascular death may be considered as death occurring within 24 hours of the first symptoms (e.g. heart attack) and usually occurs in less time. With sophisticated diagnostic techniques it is often possible to identify patients who have a high risk of sudden death. For example, modern diagnostic techniques and equipment can identify those patients having a Bifasicular Block (right bundle branch block and left axis deviation accompanied by PR prolongation and/or HV prolongation). The implantation of a pacemaker of the type described above in such a patient would monitor the patient's heart activity and remain inactive so long as the patient's heart continued to beat at a rate above a minimum rate while providing a backup for the likely cessation or reduction of the natural heart activity. The pacemaker would function in the event of a complete cessation of heart activity or the "skipping" of a single heart beat.

Pacemakers of the type described above, when implanted within a "sudden death" likely patient, have the disadvantage of operating at different standby and pacing rates once the necessity of the pacing function is indicated. That is, while the lower standby rate allows the pacemaker to monitor heart activity at a minimum rate to reduce the likelihood of competition with the heart prior to the time that the pacing function becomes necessary, sporadic natural heart activity will cause such pacemakers to periodically revert to the lower standby rate in situations where it may be desirable to monitor the heart at a rate substantially identical to the pacing rate. This, of course, can be overcome by replacing the pacemaker with one having an identity in standby and pacing rates, a typical prior art demand pacemaker, for example. However, the desirability of avoiding such a pacemaker replacement is obvious.

SUMMARY OF THE PRESENT INVENTION

The present invention provides a demand cardiac pacemaker having different standby and pacing rates and having circuitry for selectively rendering the standby and pacing rates substantially identical. Thus, the pacemaker of the present invention may be employed prophylactically to monitor heart activity in a "sudden death" patient at a first, minimum rate and provide a pacing function at a second, higher rate, while allowing the pacemaker to monitor heart activity at a rate substantially identical to the pacing rate after the necessity of the pacing function is indicated. In a preferred embodiment, first and second capacitors control the standby and pacing rates, respectively, with the charging time of the first capacitor establishing the standby rate. The second capacitor charges on the occurrence of a pacemaker output pulse and has the first capacitor within its discharge path, thereby decreasing the charge time of the first capacitor. Circuitry is provided to selectively charge the second capacitor on the occurrence of a pacemaker output pulse only or, alternatively, on the occurrence of either a pacemaker output pulse or a natural heartbeat. The pacemaker has different standby and pacing rates in the first mode and substantially identical standby and pacing rates in the second mode. In this manner, the pacemaker of the present invention may operate as a pacemaker having different standby and pacing rates during such time as that mode of operation may be advantageous with the standby rate being alterable into substantial conformity with the pacing rate when that mode of operation may be more desirable.

DETAILED DESCRIPTION OF THE DRAWINGS

Figure 1:
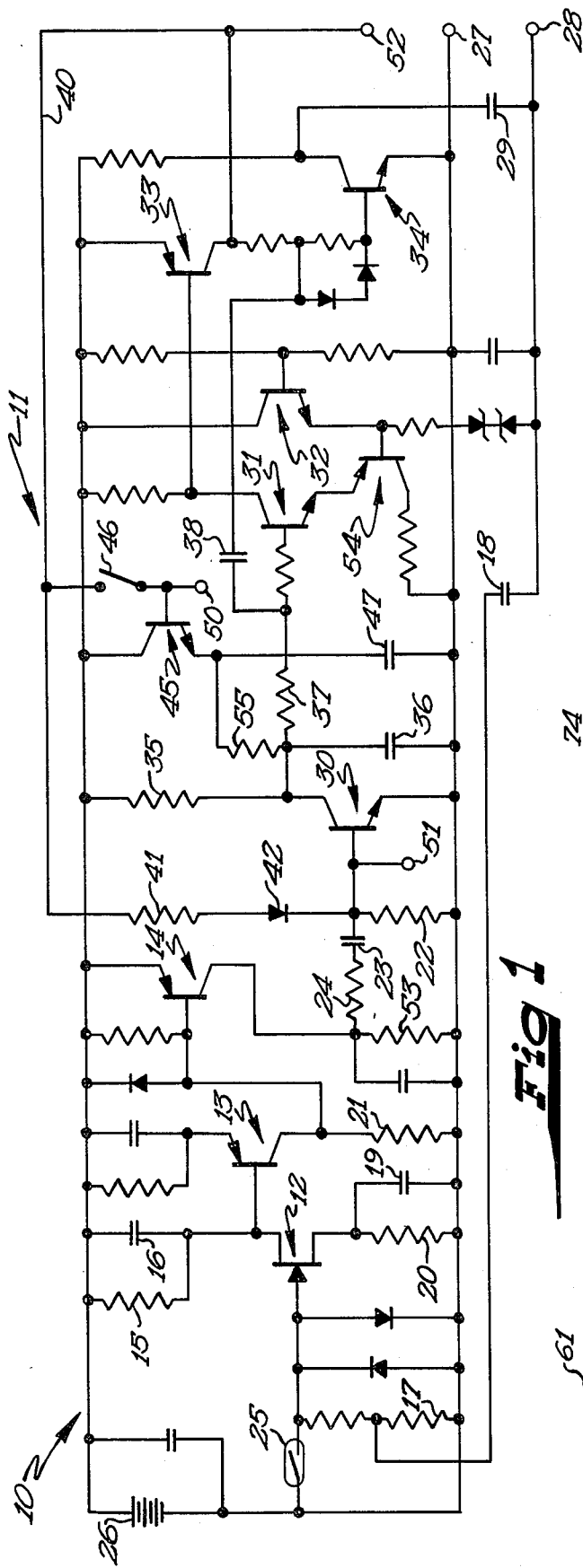
FIG. 1 illustrates a prior art cardiac pacemaker having different standby and pacing rates with modifications to render the same adaptable to the present invention.

FIG. 1 illustrates a prior art cardiac pacemaker having different standby and pacing rates with modifications to accommodate the standby rate altering system of the present invention. The pacemaker of FIG. 1 includes an amplifier section and pulse generator section shown generally at 10 and 11, respectively. Briefly, the amplifier section includes transistors 12, 13 and 14 and their associated components. Resistance 15 and capacitance 16 operate as a filter as do resistance 17 and capacitance 18, in known manner. Also, capacitance 19 and resistance 20 provide refractory control within the amplifier section 10 and resistance 21 may be selected to establish any desired amplifier sensitivity. Reversion to asynchronous or continuous operation in the presence of interference is effected through resistances 22, 24 and 53 and capacitance 23, while reed switch 25 may be employed to select an asynchronous mode of operation. The designated elements described to this point, and the functions they perform in cooperation with the other depicted elements, are known to the prior art and form no part of the present invention beyond the necessity of providing an operative amplifier section 10. A power source 26, such as batteries, is provided to power both the amplifier section 10 and pulse generator section 11 and terminals 27 and 28 are adapted for connection to the heart, in known manner, to provide cardiac stimulating pulses thereto as well as to sense natural heartbeats and provide an indication of the same to the amplifying section 10. An output capacitor 29 is provided for reasons well known to those familiar with the art.

The pulse generator section 11 includes transistors 30, 31, 32, 33 and 54 while transistor 34 functions as an output transistor. As will be described more fully below, the basic rate of the pulse generator section 11 is established by the resistor 35 and capacitor 36 while the resistor 37 and capacitor 38 control the pulse generator output pulse width. Of course, the elements of the pulse generator section 11 described to this point function in combination with others of the depicted elements which may contribute to the determination of ultimate pulse generator output pulse rate and width. For example, the effect on pulse rate of capacitor 47 and its discharge through resistor 55 is described below.

In operation, the capacitor 36 charges through the resistance 35 until such time as the charge level of capacitor 36 is sufficient to turn on the transistor 31. The turn on point of transistor 31 is established, in known manner, by a reference voltage applied to the base electrode of transistor 32 and turn on of transistor 31 results in a turn on of transistor 33 and 54, and, ultimately, a turn on of output transistor 34 and the generation of an output pulse across the terminals 27 and 28. A line 40 connected to the collector electrode of transistor 33 transmits a signal, via resistor 41 and diode 42, to the base electrode of transistor 30 causing the transistor 30 to turn on and discharge the capacitor 36. Discharge of the capacitor 36 resets the timing cycle of the pulse generator section 11 and restarts its timing cycle. Similarly, a natural heartbeat felt across the terminals 27 and 28 results in the amplifier section 10 applying a signal at the base electrode of the transistor 30 causing it to turn on and discharge the capacitor 36 and restart the timing cycle of the pulse generator section 11. Thus, the capacitor 36 is discharged on the occurrence of either a pulse generator output pulse or a natural heartbeat, with a natural heartbeat occurring within the timing cycle of the pulse generator section 11 causing a resetting of the pulse generator and the prevention of a pulse generator output pulse in that timing cycle.

A transistor 45 has its base electrode connected to the line 40 via a switch 46 while its emitter-collector junction is connected between the positive terminal of the power source 26 and one terminal of a capacitor 47. The other terminal of the capacitor 47 is connected to the other terminal of the power source 26.

With the switch 46 closed, a signal appearing on the line 40, resulting from a turn on of the transistor 33, will cause the transistor 45 to turn on and charge the capacitor 47 while the transistor 30 turns on to discharge the capacitor 36. When the transistors 30 and 45 turn off, the capacitor 47 is charged while the capacitor 36 is discharged. The capacitor 47 discharges through resistor 55 and capacitor 36 which, thus, provides two charging paths for the capacitor 36 and results in a faster charging time for the capacitor 36 and a decrease, for one cycle, in the timing cycle of the pulse generator section 11. With the switch 46 still closed, a natural heartbeat sensed between the terminals 27 and 28 will result in a turn on of the transistor 30 while leaving the transistor 45 off. Thus, the capacitor 36 provides a basic pulse generator frequency or interpulse period in response to either a sensed natural heartbeat or a pulse generator output pulse, while the capacitor 47 charges only in response to a pulse generator output pulse to provide a hysteresis effect by increasing the pulse generator output pulse frequency and decreasing the interpulse period, for one timing cycle. With the switch 46 closed, the transistors 30 and 45, and capacitors 36 and 47, operate to provide differing pulse generator standby and pacing rates essentially as described in the embodiment of FIG. 2 of the incorporated patent.

The switch 46 illustrated in the demand cardiac pacemaker of FIG. 1 is normally closed and may be eliminated when that pacemaker is intended to operate with different standby and pacing rates. However, to accommodate the improvement of the present invention, the connection between the base electrode of transistor 45 and line 40 is eliminated, with the elimination of that connection being illustrated by the opening of the switch 46. To further accommodate the improvement of the present invention, the demand pacemaker of FIG. 1 is provided with: a terminal 50 connected to the base electrode of transistor 45; a terminal 51 connected to the base electrode of transistor 30; and a terminal 52 connected to the collector electrode of transistor 33.

Figure 2:
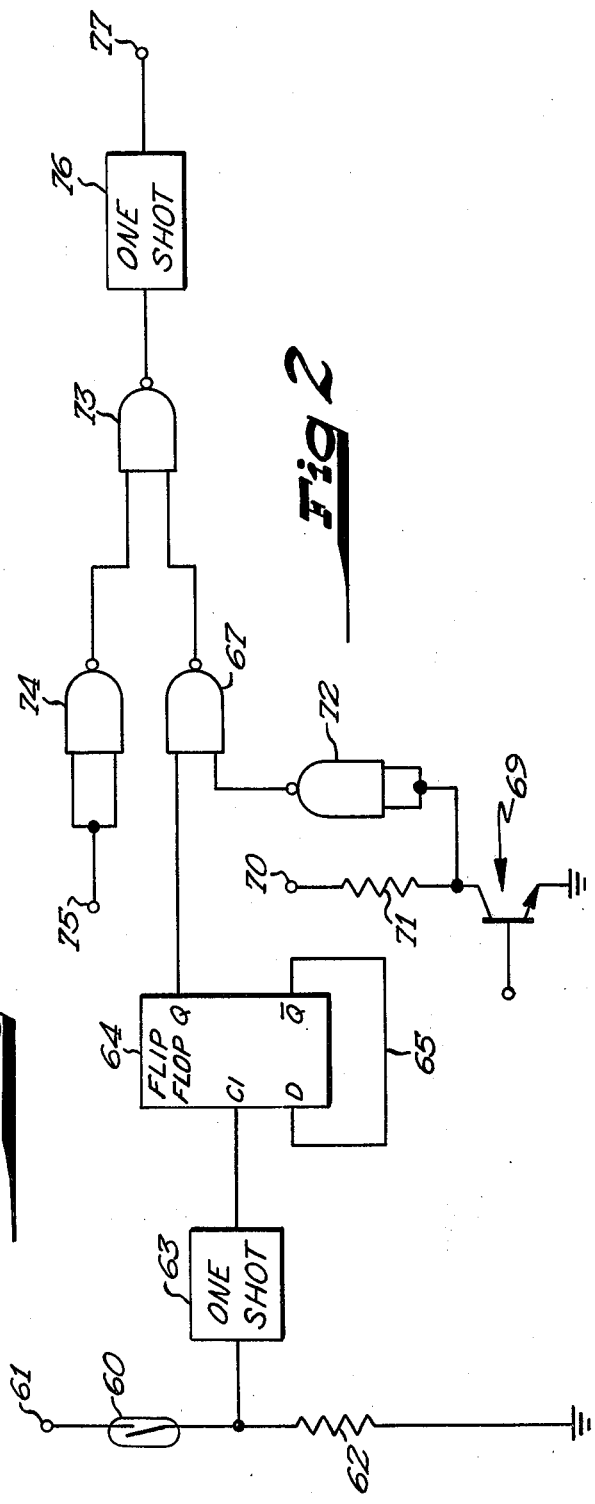
FIG. 2 illustrates a preferred embodiment of a system for altering the standby rate of the demand cardiac pacemaker of FIG. 1.

Referring now to FIG. 2, there is shown a preferred embodiment of the improvement of the present invention and its interconnection with the demand pacemaker of FIG. 1. A reed switch 60 is connected between a terminal 61 and a resistor 62. The terminal 61 is adapted for connection to the positive terminal of a power source, such as the power source 26 of FIG. 1, while the resistor 62 connects the reed switch 60 to ground. A monostable multivibrator, or one shot, 63 is connected intermediate reed switch 60 and resistor 62 and its output is connected to the clock terminal of a flip flop 64. The Q terminal of flip flop 64 is connected to its D input terminal via line 65 while the Q terminal of flip flop 64 is connected as one input to a NAND gate 67.

A terminal 68 is connected to the base electrode of a transistor 69 with the collector electrode of transistor 69 being connected to a terminal 70, through a resistor 71, and its emitter electrode being connected to ground. The terminal 70 is adapted for connection to the positive terminal of a power source, such as the power source 26 of FIG. 1, while the terminal 68 is adapted for connection to the terminal 51 of FIG. 1 such that the transistor 69 turns on and off in coincidence with the transistor 30 of FIG. 1. The collector electrode of transistor 69 is connected, through an inverter formed of NAND gate 72, as the other input of NAND gate 67. The output of NAND gate 67 is connected as one input to NAND gate 73 while the other input of NAND gate 73 is provided by an inverter formed of NAND gate 74 connected to a terminal 75. The terminal 75 is adapted for connection to the terminal 52 connected to the collector electrode of the transistor 33 of FIG. 1. The output of NAND gate 73 is connected to a monostable multivibrator, or one shot, 76 whose output is connected to a terminal 77. The terminal 77 is adapted for connection to the terminal 50 and the base electrode of transistor 45 in FIG. 1.

In operation, and assuming the Q terminal of flip flop 64 to be high, a pulse generator output signal will result in the appearance of a high signal at each of the terminals 68 and 75. The high appearing on the terminal 68 will cause the transistor 69 to turn on and apply a low signal to the inputs of the NAND gate 72. This low signal will be inverted by the NAND gate 72 to appear as a high input to the NAND gate 67. The high inputs to the NAND gate 67, from the Q terminal of flip flop 64 and the NAND gate 72, will produce a low output from the NAND gate 67 and a low input to one input terminal of the NAND gate 73. The high input applied to the terminal 75 will be inverted by the NAND gate 74 resulting in a second low input to the NAND gate 73 and a high output from the NAND gate 73 to trigger the one shot 76. Triggering of the one shot 76 will provide a high output at the terminal 77, for the duration of the one shot signal, and will result in a turn on of the transistor 45 (see FIG. 1) and a charging of the capacitor 47. The charging of capacitor 47 will result in an increase in the pulse generator output pulse frequency as described above.

Again assuming a high output from the Q terminal of flip flop 64, a sensed natural heartbeat will be presented to the amplifying section 10 of the pacemaker of FIG. 1 to produce a high on the terminal 68. The terminal 75 will remain low. As described above, a high signal appearing on both the terminal 68 and the Q terminal of flip flop 64 results in a low output from NAND gate 67 and one low input to NAND gate 73. The low signal appearing on terminal 75 will be inverted by NAND gate 74 to provide a high input to NAND gate 73. These high and low inputs to NAND gate 73 will result in a high output from NAND gate 73 and the triggering of one shot 76 to again turn on transistor 45 and charge the capacitor 47. Thus, with the Q terminal of flip flop 64 high, the circuitry of FIG. 2 will result in substantially the same pulse generator output pulse frequency, or interpulse period, upon the occurrence of either a pulse generator output pulse or a sensed natural heartbeat. From this, it can be seen that the circuitry of FIG. 2 can be employed to modify the operation of the pacemaker of FIG. 1 to render its standby and pacing rates substantially identical. The duration of the signal from the one shot 76 controls the on time of the transistor 45 and, thus, the charge on the capacitor 47. Of course, the capacitor 47 may be selected to be substantially fully charged during the shortest of the sensed heartbeat and pulse generator output pulse, with the duration of those pulses controlling the on time of the transistor 45 directly from the output of the NAND gate 73. In this instance, the one shot 76 may be eliminated. Low signals at both the terminals 68 and 75 will result in a low signal at terminal 77.

When a magnetic field is placed in proximity to the reed switch 60, the switch 60 will close and apply the positive potential at the terminal 61 to the one shot 63 and trigger the one shot 63. The one shot output is applied as a clock pulse to the flip flop 64, with the illustrated configuration of flip flop 64 resulting in the Q terminal going low and a low input to the NAND gate 67. One low input to the NAND gate 67 will result in its having a high output without regard to the signal applied to its other input. Thus, with the Q terminal of flip flop 64 low, the circuitry of FIG. 2 is rendered insensitive to sensed heartbeats inasmuch as the signal appearing at the terminal 68 cannot alter the output of the NAND gate 67. Also, as long as the transistor 33 remains off, a low will appear at the terminal 75 and be inverted to appear as a high at the other input of NAND gate 73 to result in a low signal from the NAND gate 73 and a low signal on the terminal 77. Conversely, turn on of the transistor 33, during the generation of a pulse generator output pulse, will produce a high signal at the terminal 75 which will be inverted by the NAND gate 74 to result in a high output from the NAND gate 73 and a triggering of the one shot 76. Thus, with the Q terminal of flip flop 64 low, the circuitry of FIG. 2 allows the pacemaker of FIG. 1 to operate at different standby and pacing rates.

Successive closings of the reed switch 60 will result in successive triggerings of the one shot 63 and an alternating high and low at the Q terminal of flip flop 64 as well as an alternation of the pacemaker standby rate between a rate lower than the pacing rate and a rate substantially identical to the pacing rate. The length of the signal from the one shot 63 provides a refractory period during which closings of a reed switch 60 will be inoperative to alter the state of the flip flop 64. This refractory period provides security against a "bouncing" of the reed switch 60. The flip flop 64 acts as a memory to maintain the operating mode of the circuitry of FIG. 2 until that mode is altered by the next closing of the reed switch 60.

The NAND gate 67 and 72–74 may be identical and the circuitry of FIG. 2 has been advantageously operated with components having RCA manufacturer's designation CD 4011. Similarly, flip flop 64 may be advantageously formed of that component having RCA manufacturer's designation CD 4013.

Obviously, many modifications and variations of the present invention are possible in light of the above teachings. An example of such an obvious modification would be an application or the principles of FIG. 2 to the embodiments of FIGS. 1 and 2 of the incorporated patent to accomplish an alternating identity and difference between their standby and pacing rates. It is therefore to be understood that, within the scope of appended claims, the invention may be practiced otherwise than specifically described.

What is claimed is:

1. In a demand cardiac pacemaker of the type having input and output means adapted for connection to the heart, the input means including means for sensing natural heartbeats, having pulse generator means connected to said output means and including timing circuit means connected to said sensing means for establishing a first pulse generator means output pulse rate, and having means cooperating with said timing circuit means for providing a second, different pulse generator means output pulse rate, the improvement which comprises means operatively connected to said cooperating means for selectively rendering said first and second rates substantially identical.

2. The pacemaker of claim 1 wherein said rendering means comprises means responsive to externally generated signals for selectively altering one of said first and second rates.

3. The pacemaker of claim 2 wherein said altering means alters said second rate.

4. In a demand cardiac pacemaker of the type having input and output means adapted for connection to the heart, the input means including means for sensing natural heartbeats, having pulse generator means connected to said output means, and having means for establishing a first pulse generator means interpulse period in response to a sensed natural heartbeat and a second, different pulse generator means interpulse period in response to a pulse generator means output pulse, the improvement which comprises means for selectively altering at least one of said first and second interpulse periods to provide substantially identical interpulse periods in response to natural heartbeats and pulse generator means output pulses.

5. The pacemaker of claim 4 wherein said first interpulse period is longer than said second interpulse period and said altering means comprises means for selectively shortening said first interpulse period.

6. The pacemaker of claim 5 wherein said altering means comprises means responsive to externally generated signals for altering said first interpulse period between said longer and shortened periods on alternate external signals.

7. In a demand cardiac pacemaker of the type having input and output means adapted for connection to the heart, the input means including means for sensing natural heartbeats, having pulse generator means connected to said output means, and having timing circuit means differently responsive to natural heartbeats and pulse generator means output pulses for establishing a first pulse generator means interpulse period in response to natural heartbeats and a second pulse generator means interpulse period in response to pulse generator means output pulses, the improvement which comprises means connected to said timing circuit means and responsive to externally generated signals for selectively rendering said timing circuit means substantially identically responsive to natural heartbeats and pulse generator means output pulses.

8. The pacemaker of claim 7 wherein said timing circuit means comprises first and second capacitance means, the charging time of said first capacitance means controlling the timing of said pulse generator means output pulses and the charge on said second capacitance means controlling the charging time of said first capacitance means, and means differently responsive to natural heartbeats and pulse generator means output pulses for controlling the charge on said second capacitance means, the improvement further comprising means for selectively rendering said second capacitance means charge controlling means substantially identically responsive to natural heartbeats and pulse generator means output pulses.

9. The pacemaker of claim 8 wherein said second capacitance means charge controlling means comprises means for charging said second capacitance means in response to a pulse generator means output pulse, the improvement further comprising means for selectively charging said second capacitance means in response to a pulse generator means output pulse and a natural heartbeat.

10. The pacemaker of claim 9 wherein said means responsive to externally generated signals comprises reed switch means.

11. The pacemaker of claim 8 wherein said means responsive to externally generated signals comprises reed switch means.

12. The pacemaker of claim 8 further comprising memory means for maintaining the selected response of said second capacitance means charge controlling means between said externally generated signals.

13. In a demand cardiac pacemaker of the type having input and output means, the input means including means for sensing natural heartbeats, having pulse generator means connected to said output means, and having timing circuit means connected to said sensing means including first capacitance means for controlling the pulse generator means output pulse frequency in accordance with the first capacitance means charging time and means responsive to a pulse generator means output pulse for changing the charging time of said first capacitance means, the improvement which comprises means connected to said charging time changing means and responsive to externally generated signals for rendering said charging time changing means responsive to natural heartbeats on alternate ones of said externally generated signals.

14. The pacemaker of claim 13 wherein said charging time changing means comprises second capacitance means and means for charging said second capacitance means on the occurrence of a pulse generator means output pulse, the discharge path of said second capacitance means including said first capacitance means, the improvement further comprising means for rendering said second capacitance means charging means responsive to natural heartbeats following alternate ones of said externally generated signals.

15. The pacemaker of claim 14 further comprising memory means for switching between first and second states in response to said externally generated signals while maintaining its state between said signals and logic means responsive to the state of said memory means for enabling the charging of said second capacitance means only on the occurrence of a pulse generator means output pulse when said memory means is in said first state while enabling the charging of said second capacitance means on the occurrence of pulse generator means output pulses and natural heartbeats when said memory means is in said second state.

16. In a demand cardiac pacemaker of the type having input and output means, the input means including means for sensing natural heartbeats, having a pulse generator means connected to said output means, having first timing means for controlling the pulse generator means output pulse frequency, having means for resetting said first timing means on the occurrence of either a natural heartbeat or a pulse generator means output pulse and having means for altering said pulse generator means output pulse frequency for one pulse cycle following a pulse generator means output pulse, the improvement which comprises means interconnecting said resetting means and said altering means and responsive to externally generated signals for enabling said altering means on the occurrence of natural heartbeats and pulse generator means output pulses following alternate ones of said externally generated signals.

17. The pacemaker of claim 16 wherein said first timing means comprises first capacitance means and said altering means comprises second capacitance means and means for controlling the charging of said second capacitance means, the discharge path of said second capacitance means including said first capacitance means, the improvement further comprising memory means for switching between first and second states in response to said externally generated signals while maintaining its state between said signals and logic means responsive to the state of said memory means for enabling the charging of said second capacitance means only on the occurrence of a pulse generator means output pulse when said memory means is in said first state while enabling the charging of said second capacitance means on the occurrence of pulse generator means output pulses and natural heartbeats when said memory means is in said second state.

18. The pacemaker of claim 17 wherein said means responsive to externally generated signals comprises reed switch means for closing on the application of a magnetic field, said memory means alternately switching between said first and second states on successive closing of said reed switch means.

19. The pacemaker of claim 18 further comprising means for preventing said memory means from switching state for a predetermined time following each switch in state.

20. The pacemaker of claim 19 wherein said preventing means comprises one shot means interconnecting said reed switch means and said memory means, said memory means switching in response to the output of said one shot means.

21. In a demand cardiac pacemaker of the type having input and output means, the input means including means for sensing natural heartbeats, having pulse generator means connected to said output means, and having hysteresis means connected to said sensing means for providing different pulse generator means standby and pacing rates, the improvement which comprises means responsive to externally generated signals for selectively connecting said hysteresis means to said pulse generator means.

* * * * *